US00PP33834P3

(12) United States Plant Patent
Gray et al.

(10) Patent No.: US PP33,834 P3
(45) Date of Patent: Jan. 11, 2022

(54) FLORIBUNDA ROSE PLANT NAMED 'GRAYLW'

(50) Latin Name: ***Rosa* hybrid**
Varietal Denomination: GRAylw

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 17/300,206

(22) Filed: Apr. 13, 2021

(65) Prior Publication Data

US 2021/0321548 P1 Oct. 14, 2021

Related U.S. Application Data

(60) Provisional application No. 63/009,528, filed on Apr. 14, 2020.

(51) Int. Cl.
*A01H 6/74* (2018.01)
*A01H 5/02* (2018.01)

(52) U.S. Cl.
USPC ..... Plt./145
CPC ..... *A01H 6/749* (2018.05)

(58) Field of Classification Search
USPC ..... Plt./145
See application file for complete search history.

*Primary Examiner* — Annette H Para
(74) *Attorney, Agent, or Firm* — Samuel R. McCoy, Jr.

(57) ABSTRACT

'GRAylw' is a new and distinct floribunda type *Rosa* hybrid cultivar which is characterized by the combination of an upright to semi-weeping, bushy growth habit, nearly continuous flowering, with flowers that exhibit a distinct strong, bright yellow color and moderate to strong fragrance and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAylw'.

BACKGROUND OF THE INVENTION

Parentage: 'GRAylw' is a seedling selection which resulted from the controlled cross-pollination of an unnamed *Rosa* hybrid female breeding line (not patented) and an unnamed *Rosa* hybrid male breeding line (not patented). Both parents, developed by the same inventor and never commercially released, exhibited traits deemed commercially significant and desirable.

After many years of trialing, the female parent was confirmed to possess a combination of desirable traits such as very strong fragrance and having flower color white, borne on a bushy plant growing to 1.2 m tall and wide. The male parent was selected for use in breeding after trialing confirmed the presence of a modern flower color. During the spring of 2015, the female parent was emasculated and was manually pollinated with pollen from the male parent. In winter of 2016, seed was collected from hips produced by the female parent and a number of seedlings were grown to a mature size, including the claimed plant. These progeny were further evaluated for desirable traits such as black spot disease resistance and original flower color, and in January of 2017 the claimed plant was first observed. In March of 2018, after further evaluation for desirable traits, the claimed plant was deemed to be garden-worthy and suited to widespread cultivation.. It was given the denomination 'GRAylw'.

Asexual Reproduction: Asexual propagation of 'GRAylw', by way of softwood stem cuttings, was first performed in May of 2017 at the inventor's nursery in Highfields, Australia. Through more than twelve subsequent generations, the unique features of this cultivar rave proven to be stable and true to type.

SUMMARY OF THE INVENTION

The following characteristics have been repeatedly observed and represent the distinguishing characteristics of the new *Rosa* cultivar 'GRAylw'. These traits, in combination, distinguish 'GRAylw' as a new and distinct cultivar.

1. *Rosa* hybrid 'GRAylw' exhibits an upright to semi-weeping growth habit; and
2. *Rosa* hybrid 'GRAylw' flowers exhibit a distinct strong, bright, yellow
3. *Rosa* hybrid 'GRAylw' exhibits nearly continuous flowering; and
4. *Rosa* hybrid 'GRAylw' exhibits a double flower type; and
5. *Rosa* hybrid 'GRAylw' exhibits moderate to strong rose fragrance.

DETAILED BOTANICAL DESCRIPTION

Figure 1:
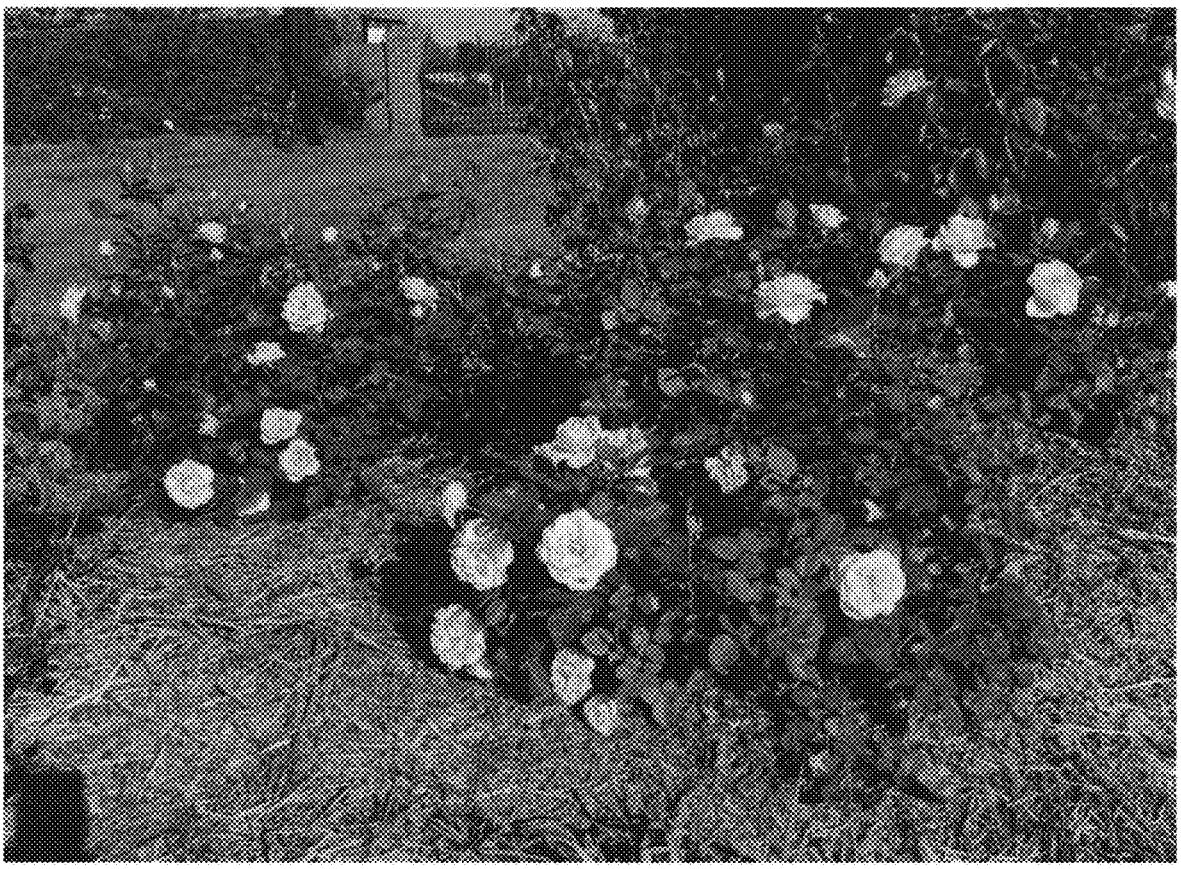
FIG. 1 illustrates, as nearly true as it is reasonably possible to make the same in color photographs of this type, an exemplary 6 month old 'GRAylw' plant grown outdoors at the inventor's commercial nursery in Highfields, Australia.
Figure 2:
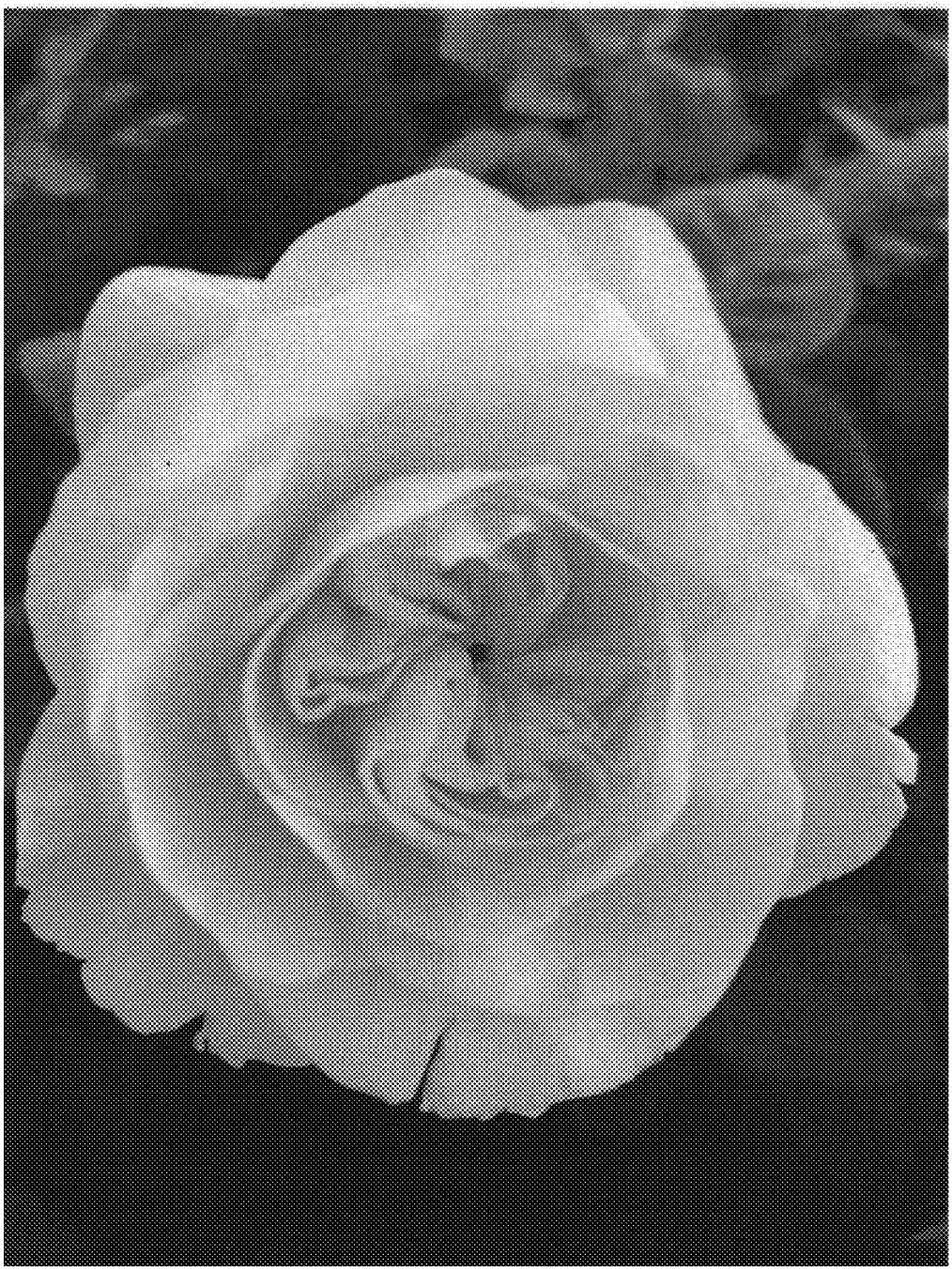
FIG. 2 illustrates, as nearly true as it is reasonably possible to make the same in color photographs of this type, the typical flower of 'GRAylw'.

The following observations and measurements, made in March of 2020, describe averages of two own-root specimens of one year old 'GRAylw' plants. The plants were grown outdoors in a garden bed of a red krasnozem soil in full sunlight, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRAylw' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2007 Fifth Edition except where common terms of color are used.

A botanical description of 'GRAylw' and comparisons with the parents and the most similar commercial cultivar of *Rosa* hybrid are provided below.

General plant description:

*Growth habit*.—Upright to semi-weeping.

*Growth rate*.—Approximately 8 months to reach 50 cm.

*Dimensions*.—80 cm tall and 60 cm wide.

*Environmental tolerance*.—Very good heat tolerance; cold hardiness is unknown.

*Disease resistance*.—Excellent resistance to powdery mildew (*Sphaerotheca pannosa*) and very high resistance blackspot (*Diplocarpon rosae*).

*Propagation*.—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit*.—Irregular branching from mature branches, breaking first from the uppermost buds near the apex of each shoot.

*Quantity*.—Numerous.

*General dimensions*.—Approximately 60 cm long; 1.0 cm in diameter near the base and tapering to 0.4 cm.

*Immature branches*.—Diameter — Approximately 0.5 cm. Texture and pubescence — Smooth with prickles; glabrous. Color — Near RHS 154B with anthocyanin present. Prickles — Density — Sparse to moderate. Color — Near RHS 29D. Shape — Convex. Texture — Smooth.

*Mature branches*.—Diameter — Approximately 0.8 cm, after one year. Texture and pubescence — Smooth with prickles; glabrous. Color — Near RHS 144C. Prickles — Density — Sparse to moderate. Color — Near RHS 145D. Shape — Convex. Texture — Smooth.

Leaves:

*Arrangement*.—Alternate imparipinnate compound leaves.

*Quantity*.—Approximately 7 per mature branch.

*Attachment*.—Petiolate.

*Leaf internode length*.—4.5 cm.

*Dimensions*.—Approximately 11 cm long and 8 cm wide.

*Petiole*.—Dimensions — 1.0 cm long and 0.1 cm wide. Color — Nearest to RHS 145A and margined RHS 144A. Texture and pubescence — Smooth and glabrous. Prickles — Present. Stipitate glands — Not present.

*Stipule*.—Dimensions — 1.0 cm long and 0.4 cm wide. Color — Nearest to RHS 145B. Texture — Pubescent. Margins — Ciliate. Apex — Apiculate. Base — Winged. Prickles — Not present. Stipitate glands — Not present.

*Rachis*.—Dimensions — 2.0 cm long and 0.1 cm wide. Color — Nearest to RHS 145A. Prickles — Present. Stipitate glands — Not present.

*Leaflets*.—Quantity — 7 leaflets on axillary leaves. Dimensions — Average size of the terminal leaflet is 5.5 cm long and 4.5 cm wide. Shape — Ovate. Apex — Acute. Base — cordate. Margins — Serrated. Texture, pubescence and luster, adaxial surface — Smooth, glabrous, and semi glossy. Texture, pubescence and luster, abaxial surface — Smooth, glabrous, and matte. Juvenile foliage color, adaxial surface — Nearest to RHS 146C, with anthocyanin intonations. Juvenile foliage color, abaxial surface — Nearest to RHS 145C, with anthocyanin intonations. Mature foliage color, adaxial surface — Nearest to RHS 141B. Mature foliage color, abaxial surface — Nearest to RHS 144D. Venation — Pinnate. Venation color, adaxial surface — Nearest to RHS 144D, with midrib RHS 144C. Venation color, abaxial surface — Nearest to RHS 144B, with midrib RHS N144D. Petiolule — Dimensions — 0.2 cm long and 0.1 cm wide. Color — Near RHS 56B with anthocyanin intonations present. Prickles — Not present. Texture — Smooth.

Inflorescence:

*Inflorescence type*.—Flowers are clustered.

*Blooming habit*.—Almost continuous from October through June in the southern hemisphere.

*Time to flower*.—6 to 8 weeks for a new stem to mature and flowering begins to occur once a stem matures.

*Peduncle*.—Dimensions — 7.0 cm long and 0.3 cm in diameter. Color — Nearest to RHS 152D with no anthocyanin present. Strength — Strong. Texture and pubescence — Smooth and glabrous. Prickles — Not present.

Bud:

*Shape*.—Ovate.

*Size*.—2.0 cm long and 1.5 cm in diameter.

*Color*.—Near RHS 144C with no anthocyanin present.

Flower:

*Calyx*.—General — Comprised of five polysepalous sepals. Diameter of calyx — 0.6 cm. Sepals — Color, interior surface — RHS 145A. Color, exterior surface — RHS 144B with anthocyanin.

Dimensions — 3.5 cm long and 1.0 cm wide. Apex — Apiculate. Base — Flat at union with receptacle. Quantity — Five. Pubescence — Densely puberulent. Margins — Entire. Stipitate glands — Not present.

*Corolla*.—General shape of corolla — Cupped and irregularly-rounded with a tight outer whorl. Rate of opening — 6 days from bud to anthesis. Dimensions — Approximately 10 cm in diameter and 5.0 cm deep. Fragrance — Moderate to strong rose scent. Lastingness — On the plant for 5 days after anthesis. Persistence — Self-cleaning. Petals — Petal count — Exhibits double flowers with approximately 27 petals under normal conditions. Petal arrangement — Irregularly rounded whorl at anthesis and aging to a loose whorl. Dimensions — 4.0 cm long and 4.0 cm wide. Petal shape — Obovate. Apex — Obcordate. Base — Flattened, then obtuse. Petal reflex — Slightly reflexed at apex. Petal margin — Entire; slightly undulating. Texture — Soft. Aspect — Formal. Petal color, upon opening — Upper surface — Nearest to RHS 5C becoming 9A at base. Lower surface — Nearest to RHS 6B. Petal color, at anthesis — Upper surface — Nearest to RHS 4D becoming 5B at base. Lower surface — Nearest to RHS 6D. Fading — Nearest to RHS 9D.

Reproductive organs:

*Stamens*.—Quantity — Approximately 50. Anthers — Shape — Narrow ovate. Length — 0.1 cm. Color — Nearest to RHS 5A. Pollen — Abundant. Pollen Color — Nearest to RHS 3A. Filaments — Color — Nearest to RHS 7A. Length — Approximately 0.8 cm.

*Pistils*.—Quantity — Approximately 50. Length — Approximately 1.0 cm. Stigma — Shape — Ovate. Color — Nearest to RHS 11B. Style — Length — Approximately 0.8 cm long. Color — Nearest to RHS 18C.

*Ovary*.—Dimensions — 0.5 cm long and 0.3 cm wide. Color — Nearest to RHS 3D.

*Receptacle*.—Shape — Pitcher-shaped. Dimensions — 0.5 cm high and 0.5 cm wide. Color — Nearest to RHS 141D.

Hip and seed:

*Hip*.—Shape — Rounded. Dimensions — 1.0 cm long and 1.0 cm wide. Texture — Smooth. Color — Nearest to RHS 142C.

*Seed*.—Shape — Rounded. Dimensions — 1.0 cm long and 1.0 cm wide. Color — Nearest to RHS 144D.

COMPARISONS WITH THE PARENTS

The new rose plant 'GRAylw' may be distinguished from its seed parent, an unnamed breeding line, by the following combination of characteristics:

1. The flowers of 'GRAylw' exhibit a distinct strong, bright yellow coloration, whereas the flowers of the seed parent exhibit an orange yellow coloration.
2. 'GRAylw' exhibits leaves semi glossy dark green, whereas the seed parent has glossy mid-green leaves.
3. 'GRAylw' has moderate to strong rose fragrance, whereas the seed parent has no fragrance.

The new rose plant 'GRAylw' may be distinguished from its pollen parent, an unnamed breeding line, by the following combination of characteristics:

1. The flowers of 'GRAylw' exhibit a distinct strong yellow coloration, whereas the flowers of the pollen parent exhibit a strong yellow coloration with red edged petals.
2. 'GRAylw' exhibits leaves semi glossy dark green, whereas the seed parent has glossy mid-green leaves.
3. 'GRAylw' has moderate to strong rose fragrance, whereas the seed parent has no fragrance.

COMPARISONS WITH THE MOST SIMILAR VARIETY OF COMMON KNOWLEDGE

Plants of the new cultivar 'GRAylw' may be distinguished from the commercial variety *Rosa* hybrid 'RADrazz' by the following combination of characteristics:

1. The flowers of 'GRAylw' are distinct strong, bright yellow coloration, whereas the flowers of 'RADrazz' are a uniform dark pink to cerise coloration.
2. Growth of 'GRAylw' is upright to semi-weeping with bushy growth, whereas 'RADrazz' growth is upright.
3. 'GRAylw' has moderate to strong rose fragrance, whereas 'RADrazz' has no fragrance.

That which is claimed:

1. A new and distinct variety of *Rosa* hybrid plant named 'GRAylw', as described and illustrated herein.

* * * * *